United States Patent [19]

Matsutani et al.

[11] Patent Number: 5,022,579
[45] Date of Patent: Jun. 11, 1991

[54] SURGICAL STAPLER

[75] Inventors: Kanji Matsutani, Tochigi; Masatoshi Fukuda, Utsunomiya, both of Japan

[73] Assignee: Matsutani Seisakusho Co., Ltd., Takanezawa, Japan

[21] Appl. No.: 389,353

[22] Filed: Aug. 3, 1989

[30] Foreign Application Priority Data

| Aug. 9, 1988 | [JP] | Japan | 63-197262 |
| Oct. 14, 1988 | [JP] | Japan | 63-257340 |
| Nov. 25, 1988 | [JP] | Japan | 63-297380 |

[51] Int. Cl.$^5$ ............................................ A61B 17/068
[52] U.S. Cl. .................................... 227/177; 227/129
[58] Field of Search .................. 227/177, 176, 175, 19, 227/120, 129, 139

[56] References Cited

U.S. PATENT DOCUMENTS

| 4,109,844 | 8/1978 | Becht | 227/120 |
| 4,493,322 | 1/1985 | Becht | 227/177 |
| 4,523,707 | 6/1985 | Blake, III et al. | 227/19 |
| 4,592,498 | 6/1986 | Braun | 227/19 |
| 4,596,350 | 6/1986 | Smith et al. | 227/19 |
| 4,789,090 | 12/1988 | Blake, III | 227/19 |

*Primary Examiner*—Douglas D. Watts
*Assistant Examiner*—Rinaldi Rada
*Attorney, Agent, or Firm*—Fish & Richardson

[57] ABSTRACT

There is disclosed a surgical stapler. An anvil is mounted on a distal end portion of an elongated body of the stapler. A guide member supports a number of staples disposed in contiguous relation to one another. The staples are urged toward the anvil by an urging mechanism. A ram is mounted on the body for movement along the longitudinal axis of the body. A lever is pivotally mounted on the body, and the pivotal movement of the lever is converted into a rectilinear movement of the ram by a motion converting mechanism. The ram, when advanced, cooperates with the anvil to deform the staple disposed in a path of movement of the ram. In order to achieve a lightweight and small-size construction of the stapler, the lever is pivotally connected at its proximal end to the proximal end portion of the body so that the lever is pivotally movable toward and away from the body, and a distal end portion of the lever serves as a manipulating portion. A mid portion of the lever spaced apart from the manipulating portion acts on the motion converting mechanism. Also, in order to achieve the above purpose, a guide passage for guiding an urging member of the urging mechanism has a curved portion, and the urging member has a flexible portion which can be guided by the curved portion.

11 Claims, 8 Drawing Sheets

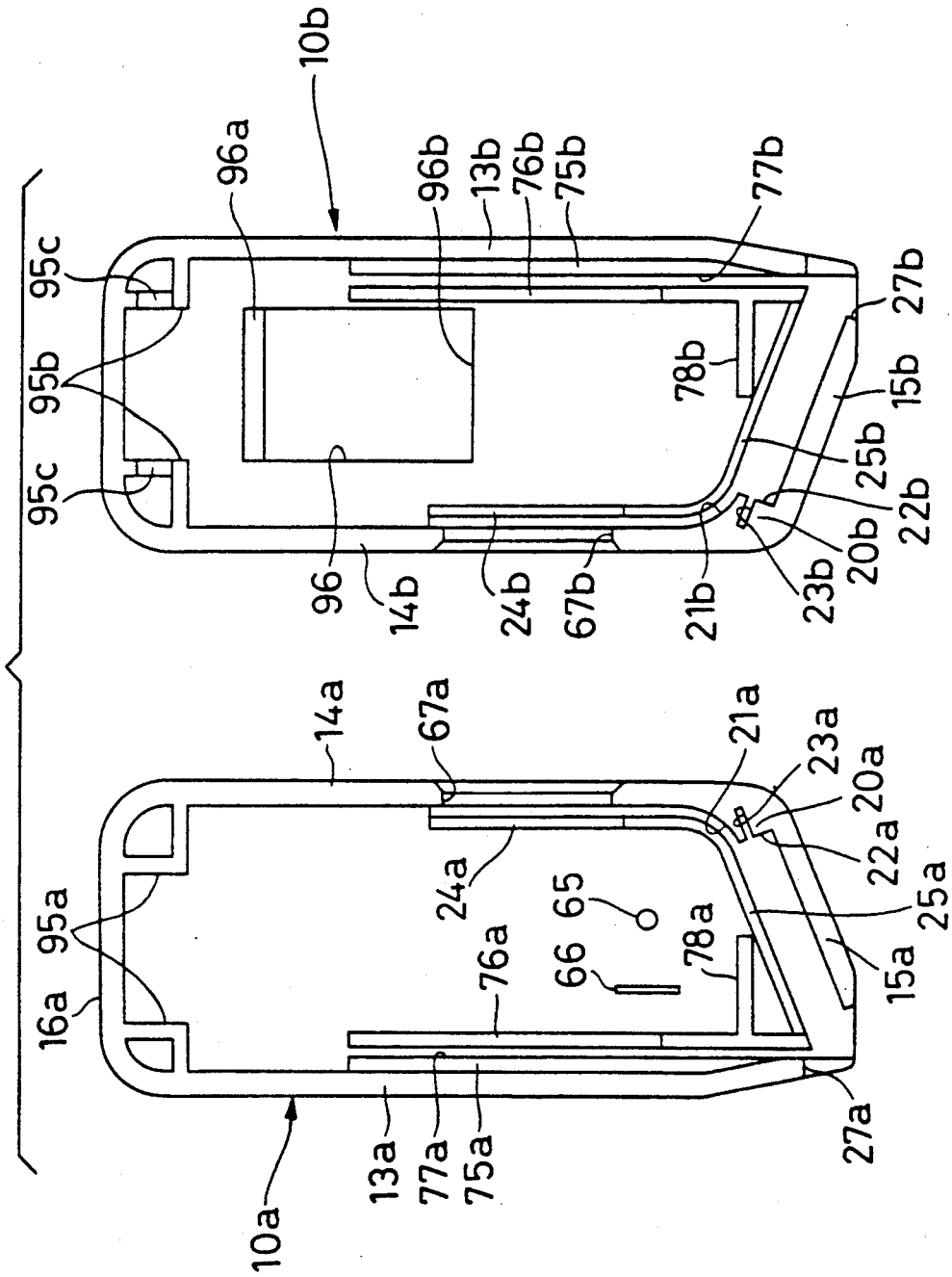

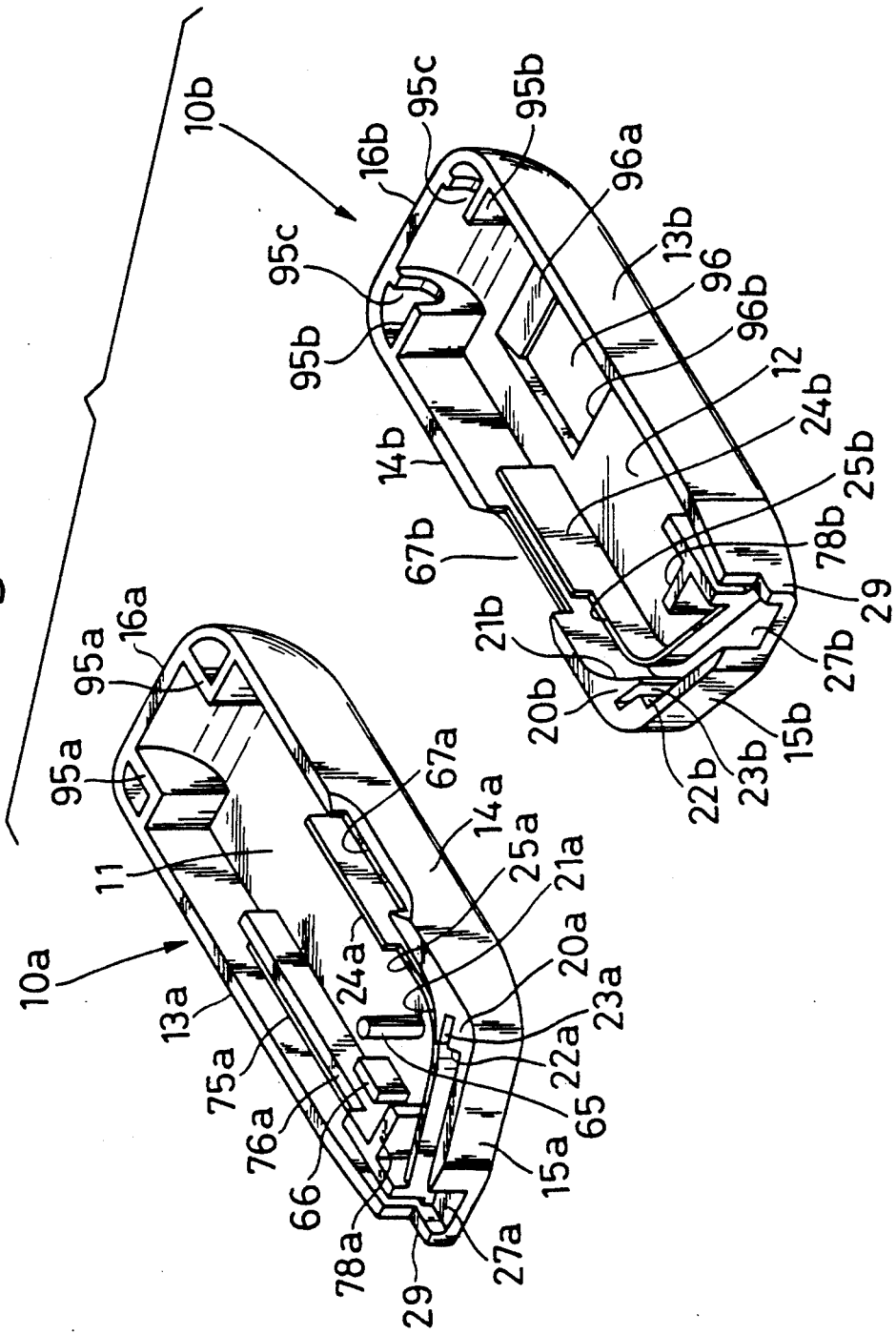

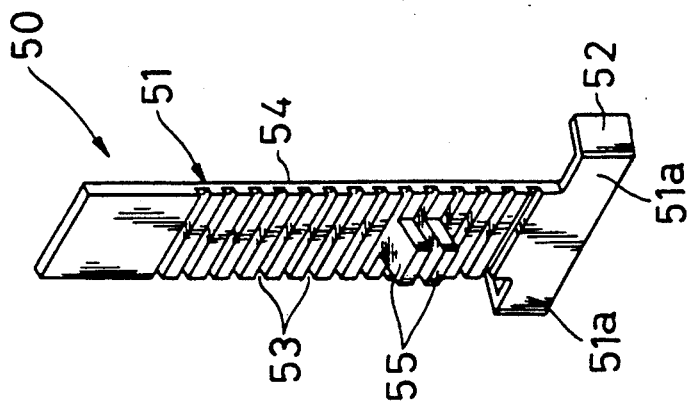
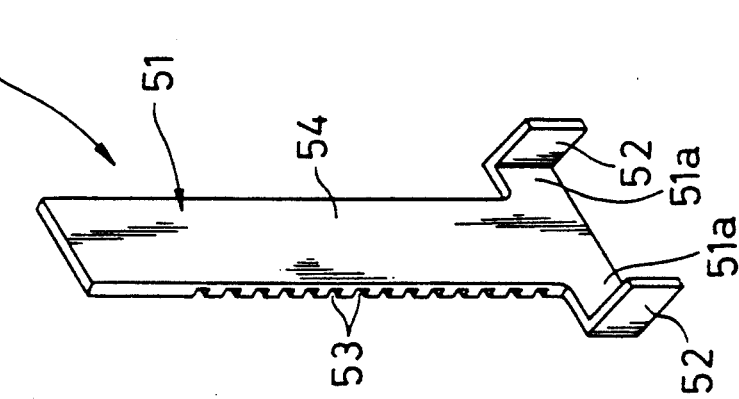
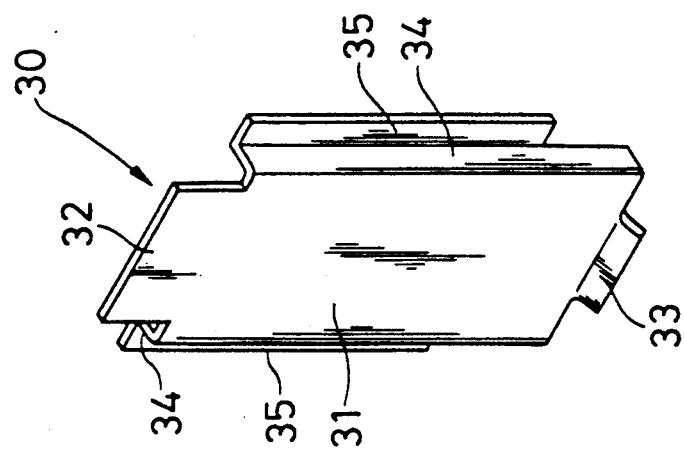

SURGICAL STAPLER

BACKGROUND OF THE INVENTION

1. Field of the Invention

This invention relates to a surgical stapler for suturing or sewing up a wound or the like.

2. Prior Art

Japanese Laid-Open (Kokai) Patent Application No. 64782/76 (corresponding to U.S. patent application Ser. No. 516,112 filed Oct. 18, 1974), Japanese Patent Publication No. 4535/86 (corresponding to German Patent Application No. 3204522.0 filed Feb. 10, 1982) and Japanese Patent Publication No. 37983/87 (corresponding to U.S. patent application Ser. No. 374,692 filed May 4, 1982) disclose gun-shaped staplers. Such a conventional stapler comprises a body having a grip portion and an elongated portion extending generally perpendicularly from one end of the grip portion. A ram is mounted within the elongated portion so as to be slidable along the length of the elongated portion. A trigger member is movably supported on the grip portion. When the trigger member is urged toward the grip portion, the force thus applied to the trigger member is transmitted to the ram through a force-increasing means mounted within the body, so that the ram advances to cooperate with an anvil, mounted at the distal end of the elongated portion, to deform a staple. Such a conventional stapler is disadvantageous in that it is of a large size and heavy in weight.

Japanese Patent Publication No. 6773/81 corresponding to U.S. patent application Ser. No. 742,843 filed Nov. 18, 1976), Japanese Patent Publication No. 38692/86 (corresponding to U.S. patent application Ser. No. 229,080 filed Jan. 28, 1981) and Japanese Patent Publication No. 36694/87 (corresponding to U.S. patent application Ser. No. 961,740 filed Nov. 17, 1978) disclose staplers which comprise an elongated body and a lever which are pivotally connected together at their distal ends. The distal end of the lever is engaged with a ram. When the lever is urged toward the body while the lever and the body are gripped by the operator, the ram is advanced through the leverage of the lever under a strong force, so that the ram cooperates with an anvil to deform a staple. This type of conventional stapler is also disadvantageous in that it is of a large size and heavy in weight.

A lightweight and small-size stapler is disclosed in Japanese Patent Publication No. 164050/84 (corresponding to U.S. patent application Ser. No. 470,066 filed Feb. 28, 1983). This conventional stapler comprises an elongated body, and a drive member (which corresponds to the lever of the above-mentioned conventional staplers) which is foldable at its mid portion so as to serve as a toggle joint mechanism. The proximal end portion of the drive member is pivotally supported by the proximal end portion of the body, and the distal end portion of the drive member is pivotally connected to a ram which is supported by the distal end portion of the body so as to be slidable along the length of the body. When the drive member is in its inoperative condition, that is, in its non-pressed condition, the drive member is held in its folded condition, with its mid portion spaced away from the body. When the mid portion of the drive member is urged toward the body by the thumb of the operator, with the index finger held against the staple body, the drive member is extended from its folded condition. As a result, the distal end of the drive member advances, so that the ram also advance to deform a staple. Since the foldable mid portion of the drive member is supported by the thumb, the stapler can not be supported by the operator in a stable manner. In addition, the staple-deforming position is considerably spaced away forwardly from the pressing force-applying position (i.e., the manipulating position), and therefore when the pressing force is applied to the drive member, the staple-deforming position may be varied.

Japanese Patent Publication No. 46854/82 (corresponding to U.S. patent application Ser. No. 899,350 filed Apr. 24, 1978 and Ser. No. 26,071 filed Apr. 3, 1979) discloses a stapler which is similar to the stapler described in the above-mentioned Japanese Patent Publication No. 164050/84 and has the same drawbacks.

A lightweight and small-size stapler is also disclosed in Japanese Laid-Open Patent Application No. 82842/84 (corresponding to U.S. patent application Ser. No. 425,542 filed Sept. 28, 1982). In this conventional stapler, a pair of levers are pivotally connected at their proximal ends to the proximal end portion of a body, and a pair of stapleforming elements are pivotally mounted on the distal end portion of the body. The distal ends of the levers are held in contact with the staple-forming elements. When the distal end portions of the pair of levers are pressed or urged by the thumb and the index finger, respectively, the staple-forming elements are pivotally moved at their one ends, so that a staple is deformed by the other ends of the staple-forming elements. This conventional stapler has no function of increasing the force applied by the operator. Therefore, this stapler is disadvantageous in that the operator is required to exert a considerable force to operate the stapler. This conventional stapler employs the staple-forming elements pivotally mounted on the body, instead of a linearly movable ram, and in this respect this stapler is different in basic construction from the stapler of the present invention.

SUMMARY OF THE INVENTION

It is therefore an object of this invention to provide a surgical stapler which can be lightweight and be of a small size, and requires less manipulating force for deforming a staple, and can deform the staple in a stable manner.

According to one aspect of the present invention, there is provided a surgical stapler comprising:

(a) an elongated body;

(b) an anvil mounted on a distal end portion of the body;

(c) means for supporting a number of staples disposed in contiguous relation to one another and for guiding the staples toward the anvil;

(d) means for urging the staples, supported on the support and guide means, toward the anvil;

(e) a ram mounted on the body so as to be movable toward and away from the anvil along a straight path extending along a longitudinal axis of the body, a leading one of the staples being disposed in the path and being disposed between the ram and the anvil;

(f) a lever pivotally connected at its proximal end to a proximal end portion of the body so as to be pivotally movable toward and away from the body, the lever having a manipulating portion at its distal end portion for pivotally moving the lever; and (g) means for converting the pivotal movement of the lever into a rectilinear movement of the ram along the path; the converting means moving the ram toward the anvil when the lever is pivotally moved toward the body, so that the ram cooperates with the anvil to deform opposite ends of the leading staple toward each other; the lever acting on the converting means at a mid portion of the lever disposed intermediate the proximal end of the lever and the manipulating portion, so that a force greater than a force applied to the manipulating portion can be applied to the ram through the leverage of the lever.

According to another aspect of the present invention, there is provided a surgical stapler comprising:

(a) an elongated body having a guide passage;

(b) an anvil mounted on a distal end portion of the body;

(c) means for supporting a number of staples disposed in contiguous relation to one another and for guiding the staples toward the anvil, the support and guide means communicating with the guide passage;

(d) means for urging the staples, supported on the support and guide means, toward the anvil, the urging means comprising an elongated urging member and a resilient member for urging the urging member toward the staples, the urging member being received in the guide passage so as to be slidingly movable along the guide passage, one end of the urging member being urged against a trailing one of the staples remote from the anvil, the guide passage having a curved portion, the urging member has a flexible portion which can be guided by the curved portion, and the resilient member being engaged with that portion of the urging member other than the one end of the urging member;

(e) a ram mounted on the body so as to be movable toward and away from the anvil along a straight path extending along a longitudinal axis of the body, a leading one of the staples being disposed in the path and being disposed between the ram and the anvil;

(f) a lever pivotally connected to the body so as to be pivotally movable toward and away from the body; and (g) means for converting the pivotal movement of the lever into a rectilinear movement of the ram along the path; the converting means moving the ram toward the anvil when the lever is pivotally moved toward the body, so that the ram cooperates with the anvil to deform opposite ends of the leading staple toward each other.

BRIEF DESCRIPTION OF THE DRAWINGS

FIG. 8 is a front-elevational view of a pair of shell halves constituting a body of the stapler, as shown in their disassembled condition;

FIG. 9 is a perspective view of the pair of shell halves as shown in their disassembled condition;

FIG. 10 is a perspective view of a guide member having an anvil portion;

FIGS. 11A and 11B are perspective views of a staple-urging member, respectively, as viewed in different directions;

DESCRIPTION OF THE PREFERRED EMBODIMENTS OF THE INVENTION

The invention will now be described with reference to the drawings.

Figure 2:
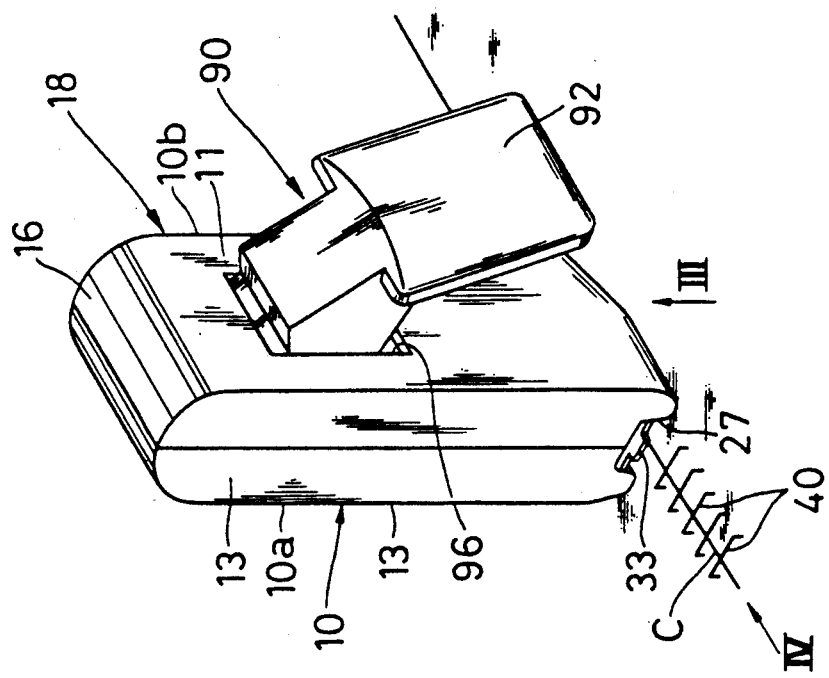
FIG. 2 is a perspective view of the stapler.
Figure 1:
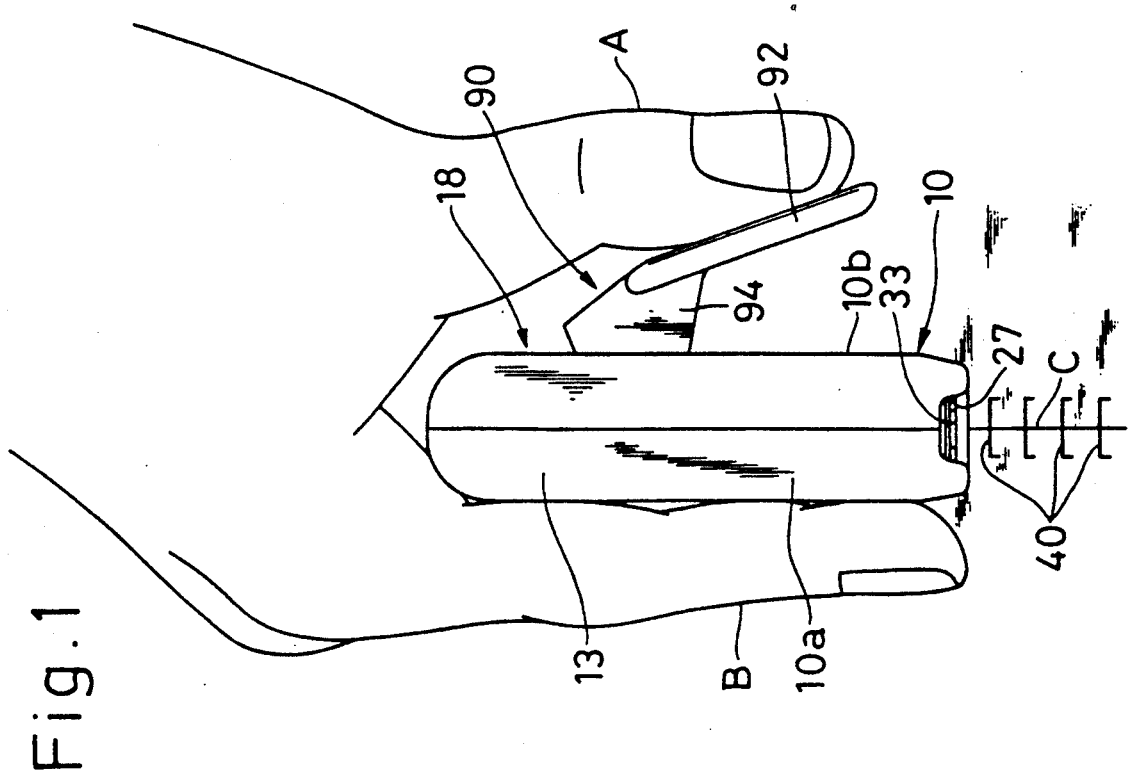
FIG. 1 is a front-elevational view of a stapler provided in accordance with the present invention, showing the manner of operating it.
Figure 5:
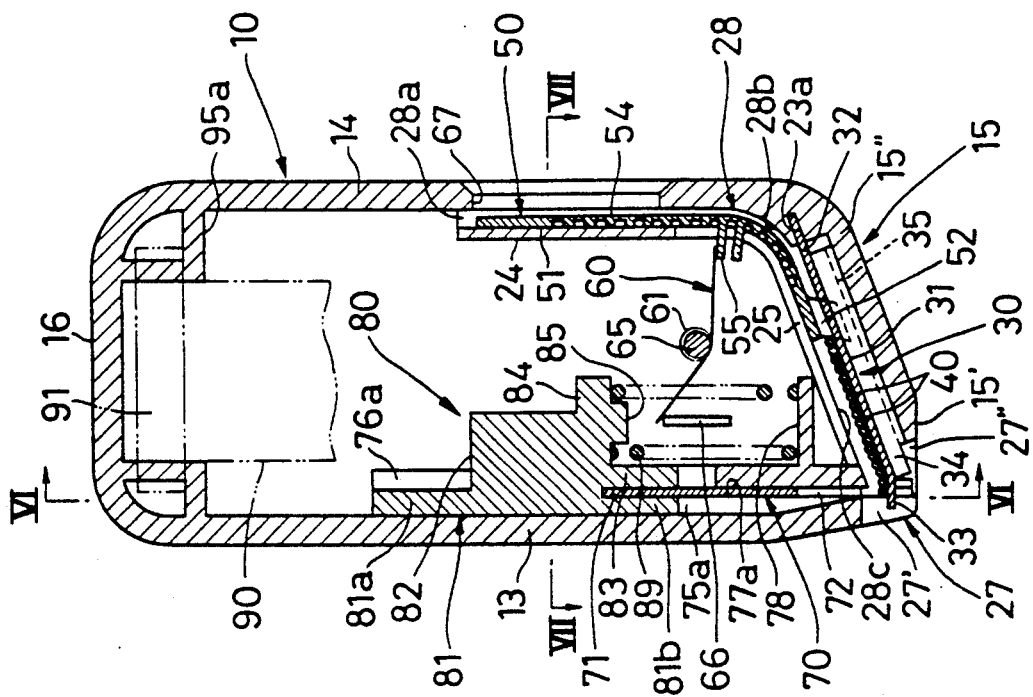
FIG. 5 is a longitudinal cross-sectional view of the stapler.

FIGS. 1 and 2 show a surgical stapler of the disposable type which comprises an elongated hollow body 10 made of a resin. The overall length of the body 10 is not more than 9 cm, and preferably 4 to 7 cm. The body 10 is composed of a pair of shell halves 10a and 10b connected together by an adhesive or the like. As best shown in FIGS. 8 and 9, the shell halves 10a and 10b are substantially symmetrical in outer shape with respect to the plane of connection between them. The shell half 10a has a substantially flat wall 11 extending in the longitudinal axis of the body 10, a pair of opposed side walls 13a and 14a formed respectively on the opposite lateral edges of the wall 11, and a pair of opposed end walls 15a and 16a formed respectively on the opposite end edges of the wall 11. The walls 13a, 14a and 15a are flat and are disposed substantially perpendicular to the wall 11. Similarly, the shell half 10b has a substantially flat wall 12 extending in the longitudinal axis of the body 10, a pair of opposed side walls 13b and 14b formed respectively on the opposite lateral edges of the wall 12, and a pair of opposed end walls 15b and 16b formed respectively on the opposite end edges of the wall 12. The walls 13b, 14b and 15b are flat and are disposed substantially perpendicular to the wall 12. The walls 11 and 12 are disposed in opposed relation to each other and serve as side walls of the body 10, respectively. As shown in FIG. 5, the walls 13a and 13b jointly constitute a continuous side wall 13 of the body 10, and similarly the walls 14a and 14b jointly constitute a continuous side wall 14 of the body 10. Thus, the body 10 has a tubular portion 18 of a rectangular cross-section defined by the side walls 11 and 12 and the side walls 13 and 14. Also, the walls 15a and 15b jointly provide a distal end wall 15 of the body 10, and the walls 16a and 16b jointly provide a proximal end wall 16 of the body 10. The distal end wall 15 of the body 10 has a first portion 15' disposed in a plane perpendicular to the longitudinal axis of the body 10, and a second portion 15" disposed in a plane inclined with respect to the longitudinal axis of the body 10. The internal angle of the intersection between the two portions 15' and 15" are less than 180 degrees.

As shown in FIGS. 8 and 9, the corner portion of the shell half 10a where the walls 15a and 14a are joined together is thickened to provide a thickened portion 20a. The thickened portion 20a has an inner curved surface 21a and an inner flat surface 22a. A mounting groove 23a for mounting a guide member 30 (later described) is formed in the flat surface 22a. An inner wall 24a is formed on the inner surface of the wall 11, and extends along the wall 15a and 14a. That portion of the inner wall 24a corresponding to the curved surface 21a is curved. The distance between the inner wall 24a and the curved surface 21a as well as the distance between the inner wall 24a and the wall 15a is smaller than the distance between the inner wall 24a and the wall 15a. A notch 25a is formed in that portion of the inner wall 24a corresponding to the curved surface 21a and the wall 15a, the notch 25a being formed in the inner edge portion of the inner wall 24a remote from the wall 11.

The other shell half 10b has a thickened portion 20b which is disposed in symmetrical relation to the thickened portion 20a with respect to the plane of connection between the shell halves 10a and 10b. Like the thickened portion 20a, the thickened portion 20b has a curved surface 21b, a flat surface 22b and a mounting groove 23b. Also, the shell half 10b has an inner wall 24b having a notch 25b, the inner wall 24b being disposed in symmetrical relation to the inner wall 24a with respect to the plane of connection between the shell halves 10a and 10b.

Figure 7:
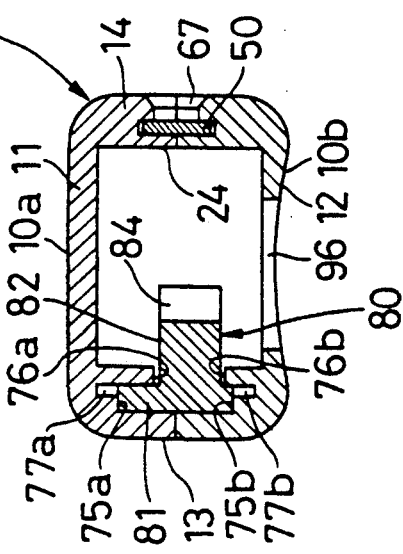
FIG. 7 is a cross-sectional view taken along the line VII—VII of FIG. 5.

The inner walls 24a and 24b are mated together at their inner edges to provide a guide wall 24 (see FIGS. 5 and 7). The guide wall 24 has a slot 25 defined by the notches 25a and 25b.

Figure 4:
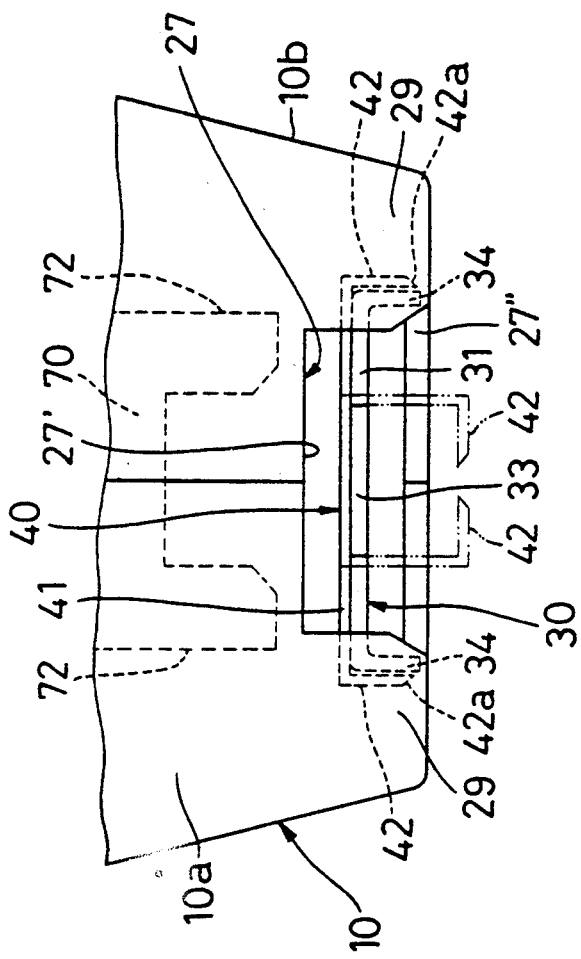
FIG. 4 is an enlarged front-elevational view of a distal end portion of the stapler as viewed in a direction of an arrow IV of FIG. 2.
Figure 3:
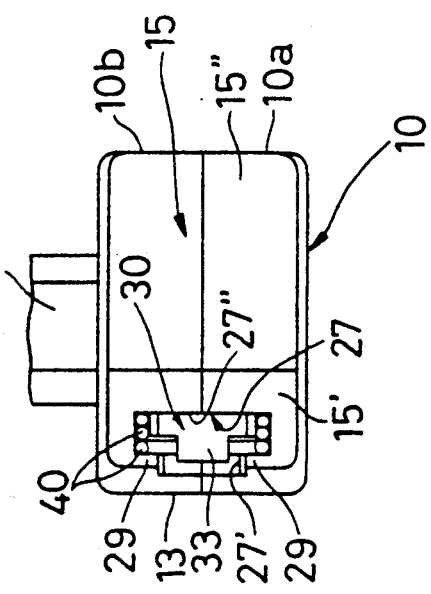
FIG. 3 is an end view of the stapler as viewed in a direction of an arrow III of FIG. 2.

As shown in FIGS. 8 and 9, a notch 27a is formed in the corner portion of the shell half 10a where the wall 13a and the wall 15a are joined together. Similarly, a notch 27b is formed in the corner portion of the shell half 10b where the wall 13b and the wall 15b are joined together, the notch 27b being disposed in symmetrical relation to the notch 27a with respect to the plane of connection between the shell halves 10a and 10b. An opening 27 defined by the two notches 27a and 27b is provided in the corner portion of the body 10 where the distal end wall 15 and the wall 13 are joined together (see FIGS. 1 to 5). The opening 27 has a first portion 27' provided in the wall 13, and a second portion 27" provided in the distal end wall 15. As shown in FIGS. 3 and 4, those portions of the wall 13 respectively disposed immediately adjacent to the opposite edges of the second portion 27" of the opening 27 serve as stoppers 29 and 29 for preventing a staple 40 from being disengaged from the body 10.

As shown in FIG. 5, the guide member 30 of steel is mounted on the body 10 adjacent to its distal end. As shown in FIG. 10, the guide member 30 has a flat base 31 of a rectangular shape, an insertion portion 32 extending from one end of the base 31 in coplanar relation thereto, and an anvil portion 33 formed on the other end of the base 31, the anvil portion 33 being inclined with respect to the base 31. A pair of leg 34 and 34 are formed respectively on the lateral edges of the base 31 and extend perpendicularly therefrom. A pair of abutment portions 35 and 35 are formed respectively on one longitudinal edges of the leg 34 and 34 remote from the base 31, and directed away from each other in parallel relation to the base 31. The guide member 30 is disposed along the distal end wall 15, with the insertion portion 32 received in the mounting grooves 23a and 23b of the shell halves 10a and 10b. The abutment portions 35 and 35 of the guide member 30 are held against the inner surface of the distal end wall 15. The anvil portion 33 of the guide member 30 is disposed in a plane perpendicular to the longitudinal axis of the body 10, and is disposed in the opening 27.

As shown in FIG. 5, a guide groove 28 is provided along the guide wall 24. The guide groove 28 has a first straight portion 28a formed by the guide wall 24 and the wall 14, a curved portion 28b formed by the guide wall 24 and the curved surfaces 21a and 21b of the shell halves 10a and 10b, and a second straight portion 28c formed by the guide wall 24 and the base 31 of the guide member 30.

A number of staples 40 are received in the second straight portion 28c of the guide groove 28, and are disposed in juxtaposed, contiguous relation to one another. As shown in FIG. 4, the staple 40 is in the form of a generally U-shaped wire, and has a straight base 41 and a pair of legs 42 and 42 respectively extending perpendicularly from the opposite ends of the base 41 in the same direction. A distal end 42a of each leg 42 is pointed. The base 41 of each staple 40 is held in sliding contact with and is guided by the base 31 of the guide member 30, the base 41 being disposed perpendicular to the longitudinal axis of the base 31. The pair of legs 42 are guided by the pair of leg 34 of the guide member 30, respectively.

An urging member 50 is received in the guide groove 28 of the body 10. The urging member 50 is made of a resin such as nylon, and has a strip-like base 51 which is greater in width at one end thereof to provide a pair of arms 51a and 51a, as shown in FIGS. 11A and 11B. A pair of abutment portions 52 and 52 extend respectively from the distal ends of the arms 51a and 51a in perpendicular relation to the base 51. A number of parallel grooves 53 are formed in one surface of that portion 54 of the base 51 lying between the opposite end portions of the base 51, and extend in the direction of the width of the base 51. The grooves 53 are spaced from one another at an equal interval along the length of the base 51. Because of the provision of the transverse grooves 53, the portion 54 is flexible. A pair of parallel opposed projections 55 and 55 are formed on the one surface of the flexible portion 54. The base 51 of the urging member 50 is received in the guide groove 28, and is slidingly movable therealong from its first straight portion 28a toward its second straight portion 28c. The abutment portions 52 and 52 of the urging member 50 are guided by the legs 34 and 34 of the guide member 30 and is held against a trailing one of the staples 40 remote from the anvil portion 33. Since the flexible portion 54 can be easily deformed or curved when it is guided by the curved portion 28b of the guide groove 28, the urging member 50 can be slidingly moved smoothly along the guide groove 28. The projections 55 and 55 extend through the slot 25, formed through the guide wall 24, inwardly of the guide wall 24, and is movable along the slot 25.

The width of the guide groove 28 is slightly greater than the thickness of the urging member 50 and the diameter of the staple 40, though this is shown in an exaggerated manner in FIG. 5 for illustration purposes.

The urging member 50 is urged by a helical spring 60 toward the anvil portion 33 of the guide member 30. More specifically, a coil portion 61 of the helical spring 60 provided at the central portion thereof is fitted on a cylindrical pin 65 formed on the shell half 10a, and one end of the helical spring 60 is engaged with a projection 66 formed on the shell half 10a whereas the other end is engaged with the projection 55 of the urging member 50.

As shown in FIGS. 8 and 9, notches 67a and 67b are formed respectively in the edges of the walls 14a and 14b of the shell halves 10a and 10b. The notches 67a and 67b jointly provide an inspection window or opening 67 (FIG. 5) through the wall 14 of the body 10. The inspection window 67 is disposed in registry with the first straight portion 28a of the guide groove 28, and the residual quantity of the staples 40 can be confirmed by viewing the position of the trailing end of the urging member 50, remote from the abutment portions 52 and 52, through the inspection window 67. A scale may be provided on the urging member 50 adjacent to its trailing end to facilitate this visual confirmation.

As shown in FIGS. 8 and 9, an elongated projection 75a is formed on the inner surface of the wall 13a of the shell half 10a and extends along the longitudinal axis of the body 10. Another elongated projection 76a is formed on the inner surface of the wall 11 of the shell half 10a and extending in parallel opposed relation to the elongated projection 75a. A guide groove 77a is formed by the two projections 75a and 76a and opens at its one end to the opening 27. The height of the projection 76a from the wall 11 is greater than the height of the projection 75a. Similarly, the other shell half 10b has elongated projections 75b and 76b and a guide groove 77b which correspond to the elongated projections 75a and 76a and the guide groove 77a and are disposed in registry with them, respectively.

Figure 12:
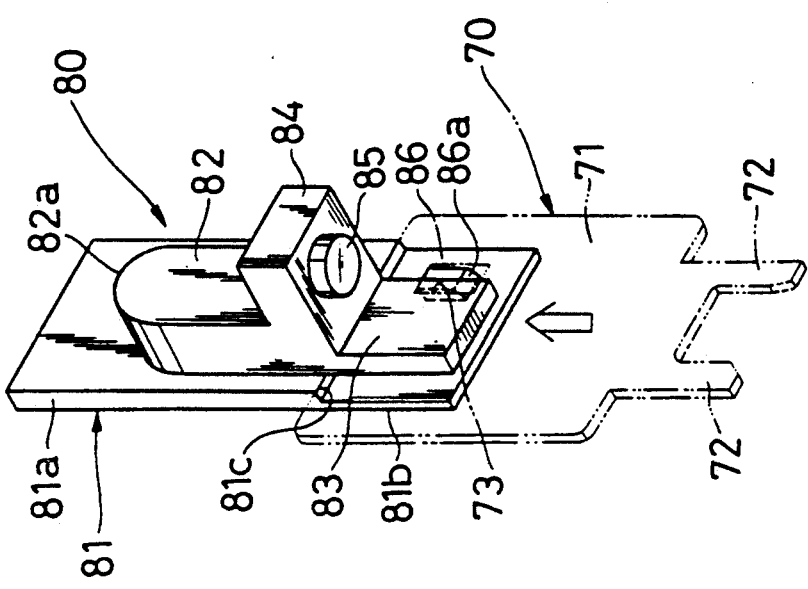
FIG. 12 is a perspective view of a cam follower.

As shown in FIG. 5, a ram 70 is received in the guide grooves 77a and 77b so as to be slidingly movable therealong. The ram 70 comprises a steel plate which has a rectangular base 71 and a pair of pressing projections 72 and 72 formed on a front end of the base 71 in parallel spaced relation to each other, as shown in FIG. 12. The distance between the pair of pressing projections 72 and 72 is greater than the width of the anvil portion 33 of the guide member 30 by an amount equal to or slightly greater than a value twice the diameter of the staple 40. When the ram 70 advances, that is, moves toward the opening 27, the pressing projections 72 and 72 press or urge the opposite end portions of the base 41 of the staple 40 placed on the anvil portion 33, so that the base 41 is bent as shown in dots-and-dash line in FIG. 4. The base 71 of the ram 70 has an engaging hole 73 formed therethrough for connecting a cam follower 80 to the ram 70.

The cam follower 80 is connected to the ram 70. As shown in FIG. 12, the cam follower 80 has a rectangular plate-like base 81 composed of a thickened portion 81a and a thinned portion 81b. A stepped portion 81c is provided between the thickened portion 81a and the thinned portion 81b. A cam receiving portion 82 is formed on one surface of the thickened portion 81a of the base 81 and extends along the longitudinal axis of the base 81. The cam receiving portion 82 has a semicylindrical end face 82a which serves as a cam receiving surface. A plate-like retainer portion 83 extends from the other end of the cam receiving portion 82 in parallel, closely spaced relation to the thinned portion 81b. A spring retainer portion 84 extends from the other end of the cam receiving portion 82 in a direction perpendicular to this portion 82. An engaging projection 85 of a cylindrical shape is formed on one surface of the spring retainer portion 84 facing away from the cam receiving surface 82a.

An engaging projection 86 is formed on one surface of the thinned portion 81b facing the retainer portion 83. This engaging projection 86 is fitted in the engaging hole 73 to thereby connect the ram 70 to the cam follower 80. Therefore, the ram 70 is moved together with the cam follower 80. For connecting the ram 70 to the cam follower 80, the base 71 of the ram 70 is first inserted into a space between the thinned portion 81b of the base 81 of the cam follower 80 and the retainer portion 83 in a direction of an arrow indicated in FIG. 12. When the rear end of the base 71 of the ram 70 remote from the pressing projections 72 and 72 is brought into engagement with a tapered surface 86a on a front end of the engaging projection 86, the thinned portion 81b and the retainer portion 83 are elastically deformed away from each other to allow the insertion of the ram 70 therebetween. When the engaging projection 86 is fitted in the engaging hole 73 of the ram 70, the thinned portion 81b and the retainer portion 83 are returned to their original shapes and are maintained parallel to each other, thus completing the connection between the ram 70 and the cam follower 80. In this condition, the rear end of the ram 70 is held against the stepped portion 81c.

As shown in FIG. 7, the outer surface of the base 81 of the cam follower 80 are held in sliding contact with the inner surface of the wall 13 whereas the inner surface of the base 81 are held in sliding contact with the elongated projections 76a and 76b at its lateral marginal portions. Therefore, the base 81 is prevented from movement in the direction of its thickness. Also, the opposite side or lateral edges of the base 81 are held in sliding contact with the elongated projections 75a and 75b, respectively, so that the base 81 is prevented from movement in the direction of its width. In other words, the cam follower 80 is movable only in the direction of sliding of the ram 70.

Spring retainer portions 78a and 78b are formed on the shell halves 10a and 10b, respectively, and cooperate with each other to provide a single spring retainer portion 78. As shown in FIG. 5, a compression coil spring 89 extends in a compressed condition between the spring retainer portion 78 and the spring retainer portion 84 of the cam follower 80. One end of the coil spring 89 is fitted on the engaging projection 85 of the cam follower 80. The cam follower 80 and the ram 70 are urged by the coil spring 89 away from the anvil portion 33 of the guide member 30.

Figure 13B:
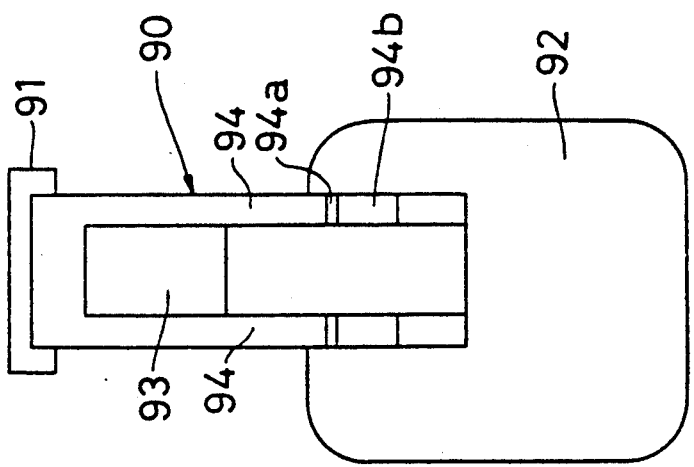
FIG. 13B is a front-elevational view of the lever.
Figure 13A:
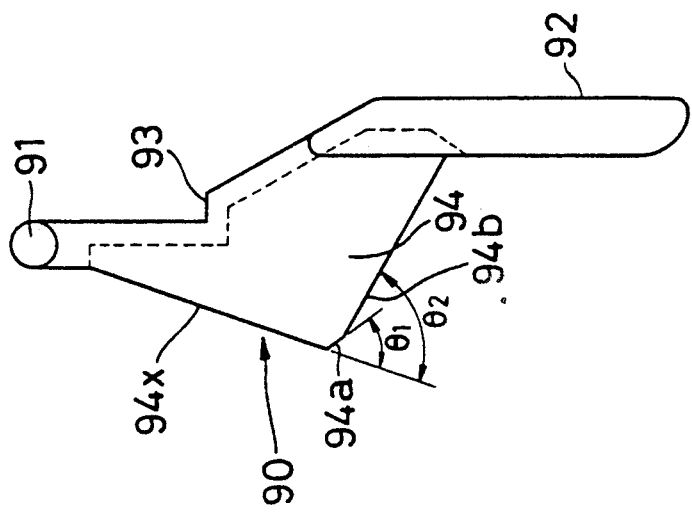
FIG. 13A is a side-elevational view of a lever.

Next, a lever 90 will now be described. The lever 90 is molded of a resin. As shown in FIGS. 13A and 13B, the lever 90 has a pivot pin portion 91 at its proximal end, a flat manipulating portion (pressure-applying portion) 92 at its distal end portion, and a plate-like connective portion 93 interconnecting the pivot pin portion 91 and the manipulating portion 92. The lever 90 further has a pair of parallel, opposed plate-like cams 94 and 94 formed on the opposite sides of the connective portion 93, the cams 94 and 94 being disposed perpendicular to the connective portion 93. The cams 94 and 94 extend to the underside of the manipulating portion 92. As shown in FIG. 13A, each cam 94 has a generally triangular shape, and has a first cam surface 94a on its edge in the vicinity of the apex of such a triangle, and a second cam surface 94b formed by the edge of the cam 94 and extending from the first cam surface 94a toward the manipulating portion 92. Each of the first and second cam surfaces 94a and 94b is flat. One side or edge 94x of the generally triangular cam 94 is disposed in a line passing through the axis of the pivot pin portion 91. The angle $\theta 2$ formed by this line and the second cam surface 94b is greater than the angle $\theta'$ formed by this line and the first cam surface 94a.

Figure 6:
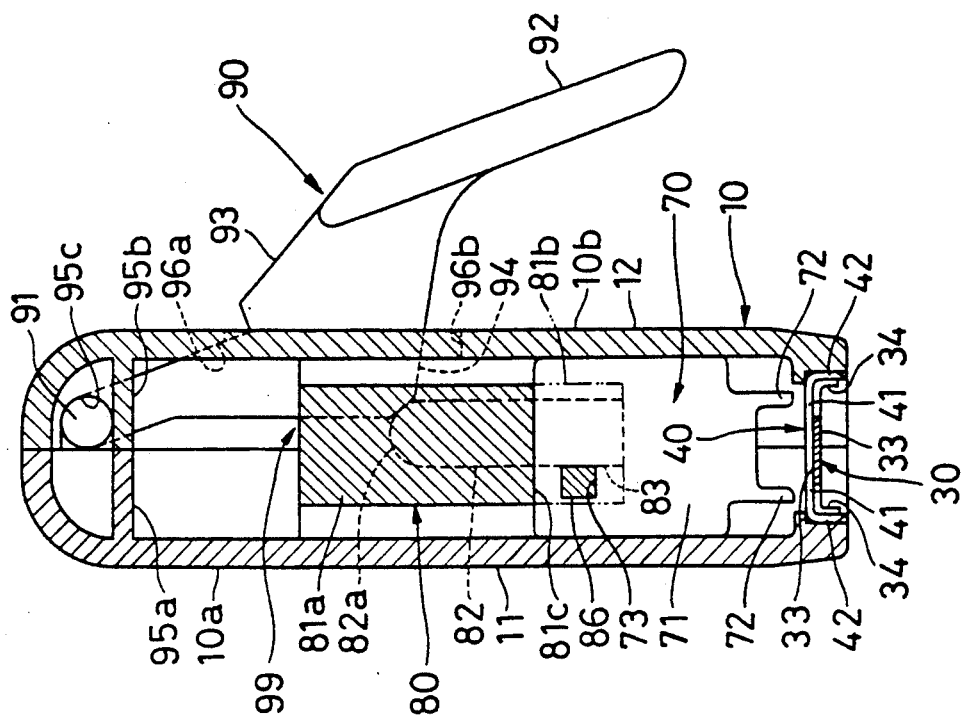
FIG. 6 is a cross-sectional view taken along the line VI—VI of FIG. 5.

The proximal end portion of the body 10 has the function of a bearing for supporting the lever 90. More specifically, as shown in FIGS. 8 and 9, a pair of bearing portions 95a and 95a are formed on the wall 16a of the shell half 10a, and also a pair of bearing portions 95b and 95b are formed on the wall 16b of the shell half 10b. A U-shaped notch 95c is formed in each of the bearing portions 95b and 95b. The notch 95c in each bearing portion 95b defines, together with its mating bearing portion 95a, a bearing hole, and as shown in FIG. 6, the opposite ends of the pivot pin portion 91 of the lever 90 are extended through these bearing holes, respectively, so that the lever 90 is pivotally supported on the body 10. An opening 96 is formed through the wall 12 of the shell half 10b, and the lever 90 extends outwardly from the body 10 through the opening 96. When the lever 90 is in its inoperative condition, that is, in its non-pressed condition, the lever 90 is extended toward the distal end of the body 10 at a predetermined angle with respect to the body 10. One edge 96a of the opening 96 disposed near the wall 16b serves as a stopper surface, the stopper surface 96a being inclined relative to the wall 12. Also, another edge 96b of the opening 96 disposed in opposed relation to the edge 96a serves as another stopper surface, the stopper surface 96b being disposed perpendicular to the wall 12. The stopper surface 96a limits the pivotal movement of the lever 90 away from the body 10 whereas the other stopper surface 96b limits the pivotal movements of the lever 90 toward the body 10. The overall length of the lever 90 is equal to or smaller (as in the illustrated embodiment) than that of the body 10. If the lever 90 is shorter than the body 10, it is preferred that the difference between the two is not more than 3 cm. The pivot pin portion 91 of the lever 90 is disposed perpendicular to the base 41 of each staple 40 and is also disposed perpendicular to the direction of movement of the ram 70.

As shown in FIG. 6, either of the first and second cam surfaces 94a and 94b of each cam 94 of the lever 90 is always disposed in tangential contact with the cam receiving surface 82a of the cam follower 80. The cams 94 and 94 of the lever 90 and the cam follower 80 jointly constitute a cam mechanism 99.

When the lever 90 is in its inoperative position, the cam follower 80 is held in its retracted position by the coil spring 89, and therefore the ram 70 is also in its retracted position and is spaced apart from the staple 40 supported by the anvil portion 33 of the guide member 30. In this condition, since the coil spring 89 acts on the lever 90 through the cam follower 80, the connective portion 93 is urged against the stopper surface 96a to thereby maintain the lever 90 at the predetermined angle with respect to the body 10, with the manipulating portion 92 considerably spaced apart from the body 10. In this inoperative condition of the lever 90, the first cam surfaces 94a and 94a of the lever 90 are held in contact with the cam receiving surface 82a of the cam follower 80.

When a wound or the like is to be sutured or sewed up by the surgical stapler of the above construction, the stapler is disposed in a generally triangular space formed by the thumb A and index finger B, for example, of the right hand of the operator, with the proximal end of the body 10 disposed at the fork portion where the thumb A and the index finger are joined together, and the thumb A is held against the manipulating portion 92 of the lever 90 whereas the index finger B (if necessary, together with the middle finger) is held against the wall 11 of the body 10. Then, the first portion 15' of the distal end wall 15 of the body 10 is brought into contact with the surface of the body of the patient in such a manner that the thumb A is directed toward the operator, with the index finger B directed away from the operator. In this condition, the opening 27 is disposed on the left side as viewed from the operator, and the view of the opening 27 (i.e., the position of deforming the staple 40) is not obstructed by the hand of the operator.

In this condition, the manipulating portion 92 of the lever 90 is pressed or urged toward the body 10 to pivotally move the lever 90 about the pivot pin portion 91. As a result, the pivotal movement of the lever 90 is converted into a rectilinear movement of the ram 70 through the cams 94 and 94 and the cam follower 80, that is, through the cam action, caused by the first cam surfaces 94a and 94a and the camreceiving surface 82a, and the subsequent cam action caused by the second cam surfaces 94b and 94 and the cam-receiving surface 82a. As a result, the ram 70 advances toward the staple 40 supported on the anvil portion 33 of the guide member 30. Since the inclination angle $\theta_1$ of each first cam surface 94a is smaller while the inclination angle $\theta_2$ of each second cam surface 94b is greater, the amount of movement of the ram 70 per unit amount of pivotal movement of the lever 90 is greater at an initial stage of this pivotal movement of the lever 90 (that is, when the first cam surfaces 94a and 94a are held in contact with the cam-receiving surface 82a). Therefore, with a small amount of the pivotal movement of the lever 90, the ram 70 can be brought into contact with the staple 40 supported on the anvil portion 33. Immediately before the ram 70 is brought into contact with the staple 40, the second cam surface 94b and 94b are brought into contact with the cam-receiving surface 82a. Then, when the lever 90 is further pivotally moved, the pressing projections 72 and 72 of the ram 70 press the staple 40 to deform it as described above. At this deforming stage, the amount of movement of the ram 70 per unit amount of pivotal movement of the lever 90 is smaller, since the second cam surfaces 94b and 94b are disposed in contact with the cam-receiving surface 82a, and the cam mechanism 99 performs a force-increasing function. The manipulating force applied to the manipulating portion 92 of the lever 90 is increased through the leverage of the lever 90 and is transmitted to the cams 94 and 94. Because of the leverage of the lever 90 and the force-increasing function of the cam mechanism 99, the deformation of the staple 40 can be achieved with a relatively small manipulating force applied by the operator.

When the cam follower 80 is urged by the pivotally-moving lever 90, the cam follower 80 is also subjected to a force acting in a direction perpendicular to the direction of sliding movement of the ram 70. However, this force is received by the elongated projections 75a and 75b through the opposite side edges of the base 81 of the cam follower 80, and therefore this force does not act on the ram 70, so that the ram 70 is prevented from deformation and is also prevented from displacing laterally out of position.

In addition, the thumb A presses against the manipulating portion 92, and this manipulating force-applying position is relatively near to the staple deforming position. Therefore, the deformation of the staple 40 can be carried out in a stable manner.

Further, the direction of movement of the manipulating portion 92 of the lever 90 toward the body 10 is the same as the direction of deformation of the pair of legs 42 and 42 of the staple 40 toward each other. Therefore, the operator feels as if he deformed the staple 40 directly by the hand, thus providing a good operability.

The pivotal movement of the lever 90 toward the body 10 is limited upon contact of the cams 94 and 94 with the stopper surface 96b of the body 10.

When the pressing or urging of the lever 90 is released, the cam follower 80, the ram 70 and the lever 90 are returned to their respective original positions under the influence of the coil spring 89.

As described above, since the stapler is of such a construction that the stapler can be held between the thumb and the index finger held respectively against the lever 90 and the body 10, the stapler can be lightweight and of a small size.

Since the guide groove 28 for guiding the movement of the urging member 50 has the curved portion 28b, the first and second straight portions 28a and 28c can be arranged in angular relation to each other so as to extend along the wall 14 and the distal end wall 15, respectively. With this arrangement, the width of the body 10 can be smaller as compared with the case where the guide groove 28 is straight over the entire length thereof. This also enables the body 10 to be lightweight and of a small size.

As shown in FIG. 4, when the base 41 of the staple 40 is bent through the cooperation of the ram 70 with the anvil portion 33, the pair of legs 42 and 42 of the staple 40 are angularly moved toward each other and are extended outwardly from the distal end wall 15 through the second portion 27" of the opening 27 formed through the body 10, so that the pair of legs 42 and 42 are put or driven into the body of the patient on the opposite sides of the wound C and is retained there.

Then, when the stapler is moved in a right-hand direction as viewed from the operater, the thus applied staple 40 is brought out of engagement of the anvil portion 33 and is discharged from the body 10 through the first portion 27' of the opening 27, so that the staple 40 remains in the body of the patient.

When the staple 40 is discharged from the anvil portion 33, the group of juxtaposed staples 40 supported on the guide member 30 are urged toward the anvil portion 33 under the influence of the helical spring 60, so that the leading staple 40 is disposed in the path of movement of the ram 70.

The above staple-applying operation is repeated, so that the staples 40 are sequentially put into the body of the patient along the wound C, thereby suturing or sewing up the wound C.

Figure 14:
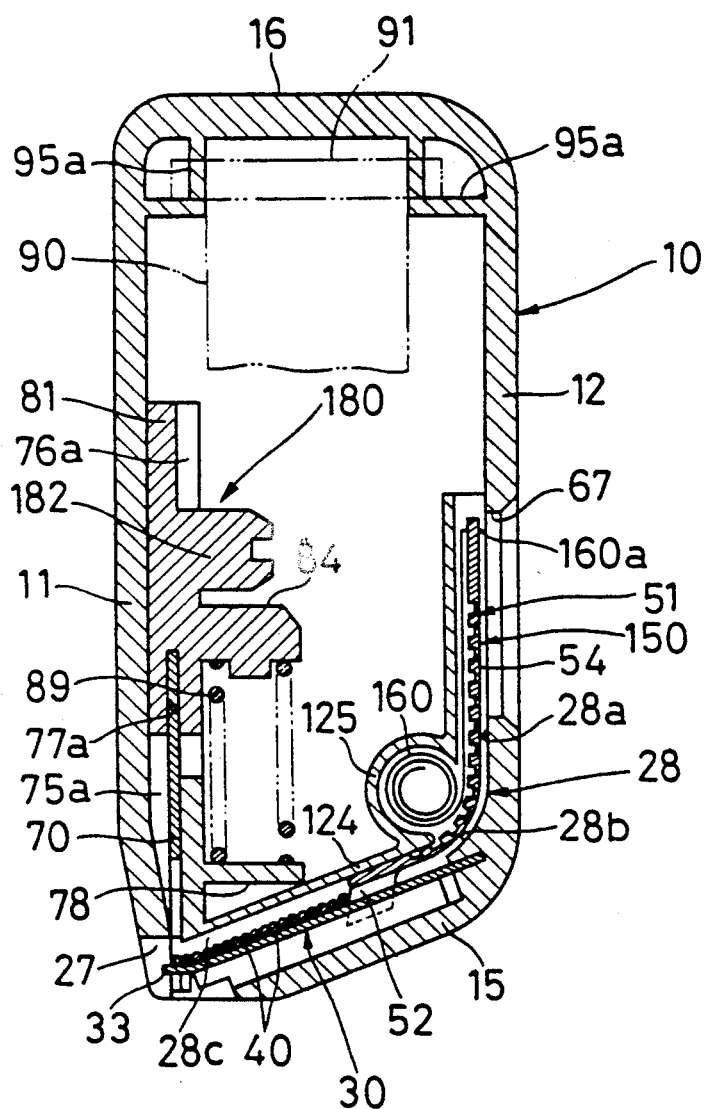
FIG. 14 is a longitudinal cross-sectional view of a modified stapler.

FIG. 14 shows a modified stapler which differs from the stapler of the preceding embodiment in that a cam-receiving portion 182 of a cam follower 180 is of a cylindrical shape, that a guide wall 124 does not have the slot 25 and instead has a rounded portion adjacent to the curved portion 28b of the guide groove 28 so as to provide a generally circular container portion 125, and that a spiral spring 160 of a strip is accommodated within the container portion 125, the spiral spring 160 having one free end. The distal end portion of the spiral spring 160 is received in and extends along the first straight portion 28a of the guide groove 28, and the other or distal end 160a of this spring is connected to the rear end of a urging member 150. More specifically, the distal end 160a of the spiral spring 160 is bent into a right-angular shape and is engaged in a hole formed through the rear end of the urging member 150. The urging member 150 is not provided with the projection 55. The urging member 150 urges the staples 40 toward the anvil portion 33 under the influence of the spiral spring 160.

The cam follower may be formed integrally with the ram. The lever may have more than two cam surfaces. Also, the cam surface may be formed by a curved surface whose radius of curvature is gradually varied.

What is claimed is:

1. A surgical stapler comprising:
   (a) an elongated body;
   (b) an anvil mounted on a distal end portion of said body;
   (c) means for supporting a number of staples disposed in contiguous relation to one another and for guiding said staples toward said anvil;
   (d) means for urging said staples, supported on said support and guide means, toward said anvil;
   (e) a ram mounted on said body so as to be movable toward and away from said anvil along a straight path extending along a longitudinal axis of said body, a leading one of said staples being disposed in said path and being disposed between said ram and said anvil;
   (f) a lever pivotally connected at its proximal end to a proximal end portion of said body so as to be pivotally movable toward and away from said body, said lever having a manipulating portion at its distal end portion for pivotally moving said lever; and
   (g) means for converting the pivotal movement of said lever into a rectilinear movement of said ram along said path; said converting means moving said ram toward said anvil when said lever is pivotally moved toward said body, so that said ram cooperates with said anvil to deform opposite ends of said leading staple toward each other; said lever acting on said converting means at a mid portion of said lever disposed intermediate the proximal end of said lever and said manipulating portion, so that a force greater than a force applied to said manipulating portion can be applied to said ram through the leverage of said lever, in which said body comprises a tubular portion of a generally rectangular cross-section having a pair of generally parallel, opposed first and second side walls, and a pair of generally parallel, opposed third and fourth side walls, and distal end wall closing a distal end of said tubular portion; there being provided an opening formed through a corner portion of said body where said first side wall and said distal end wall are joined together; said anvil being disposed in the vicinity of said opening; the opposite ends of said staple deformed by said ram and said anvil extending outwardly from said body through said opening; said deformed staple being discharged from said body through said opening; said support and guide means extending along said distal end wall; said path of movement of said ram extending along said first side wall; the axis of pivotal movement of said lever being disposed perpendicular to said first and second side walls; there being provided another opening formed through said third side wall; the proximal end portion of said lever being disposed within said body; and said lever extending outwardly from said body through said another opening.

2. A surgical stapler comprising:
   (a) an elongated body;
   (b) an anvil mounted on a distal end portion of said body;

(c) means for supporting a number of staples disposed in contiguous relation to one another and for guiding said staples toward said anvil;

(d) means for urging said staples, supported on said support and guide means, toward said anvil;

(e) a ram mounted on said body so as to be movable toward and away from said anvil along a straight path extending along a longitudinal axis of said body, a leading one of said staples being disposed in said path and being disposed between said ram and said anvil;

(f) a lever pivotally connected at its proximal end to a proximal end portion of said body so as to be pivotally movable toward and away from said body, said lever extending toward said distal end portion of said body at a predetermined angle to said body when in a non-pressed state and said lever having a manipulating portion at its distal end portion for pivotally moving said lever; and (g) means for converting the pivotal movement of said lever into a rectilinear movement of said ram along said path; said converting means moving said ram toward said anvil when said lever is pivotally moved toward said body, so that said ram cooperates with said anvil to deform opposite ends of said leading staple toward each other; said lever acting on said converting means at a mid portion of said lever disposed intermediate the proximal end of said lever and said manipulating portion, so that a force greater than a force applied to said manipulating portion can be applied to said ram through the leverage of said lever.

3. A surgical stapler according to claim 2, in which said converting means includes a cam means for increasing the force applied to said mid portion of said lever when said lever is pivotally moved toward said body and for transmitting said increased force to said ram.

4. A surgical stapler according to claim 3, in which said cam means comprises a cam formed on said mid portion of said lever, and a cam follower which is connected to said ram and is disposed in contact with said cam.

5. A surgical stapler comprising:
(a) an elongated body;
(b) an anvil mounted on a distal end portion of said body;
(c) means for supporting a number of staples disposed in contiguous relation to one another and for guiding said staples toward said anvil;
(d) means for urging said staples, supported on said support and guide means, toward said anvil;
(e) a ram mounted on said body so as to be movable toward and away from said anvil along a straight path extending along a longitudinal axis of said body, a leading one of said staples being disposed in said path and being disposed between said ram and said anvil;
(f) a lever pivotally connected at its proximal end to a proximal end portion of said body so as to be pivotally movable toward and away from said body, said lever having a manipulating portion at its distal end portion for pivotally moving said lever; and
(g) means for converting the pivotal movement of said lever into a rectilinear movement of said ram along said path; said converting means moving said ram toward said anvil when said lever is pivotally moved toward said body, so that said ram cooperates with said anvil to deform opposite ends of said leading staple toward each other; said lever acting on said converting means at a mid portion of said lever disposed intermediate the proximal end of said lever and said manipulating portion, so that a force greater than a force applied to said manipulating portion can be applied to said ram through the leverage of said lever, in which said cam has a first cam surface and a second cam surface which extends from said first cam surface toward the distal end of said lever, an amount of movement of said ram per unit amount of pivotal movement of said lever being smaller when said cam follower is disposed in contact with said second cam surface than when said cam follower is disposed in contact with said first cam surface.

6. A surgical stapler comprising:
(a) an elongated body having a guide passage;
(b) an anvil mounted on a distal end portion of said body;
(c) means for supporting a number of staples disposed in contiguous relation to one another and for guiding said staples toward said anvil, said support and guide means communicating with said guide passage;
(d) means for urging said staples, supported on said support and guide means, toward said anvil, said urging means comprising an elongated urging member and a resilient member for urging said urging member toward said staples, said urging member being received in said guide passage so as to be slidingly movable along said guide passage, one end of said urging member being urged against a trailing one of said staples remote from said anvil, said guide passage having a curved portion, said urging member having a flexible portion which can be guided by said curved portion, and said resilient member being engaged with that portion of said urging member other than said one end of said urging member;
(e) a ram mounted on said body so as to be movable toward and away from said anvil along a straight path extending along a longitudinal axis of said body, a leading one of said staples being disposed in said path and being disposed between said ram and said anvil;
(f) a lever pivotally connected to said body so as to be pivotally movable toward and away from said body; and
(g) means for converting the pivotal movement of said lever into a rectilinear movement of said ram along said path; said converting means moving said ram toward said anvil when said lever is pivotally moved toward said body, so that said ram cooperates with said anvil to deform opposite ends of said leading staple toward each other, in which said body comprises a tubular portion of a generally rectangular cross-section having a pair of generally parallel, opposed first and second side walls, and a pair of generally parallel, opposed third and fourth side walls, and a distal end wall closing a distal end of said tubular portion; there being provided an opening formed through a corner portion of said body where said first side wall and said distal end wall are joined together; said anvil being disposed in the vicinity of said opening; the opposite ends of said staple deformed by said ram and said anvil extending outwardly from said body through said opening; said deformed staple being discharged from said body through said opening; said support and guide means extending along said distal end wall; said path of movement of said ram extending along said first side wall; said curved portion of said guide passage being disposed in the vicinity of a corner portion of said body where said second side wall and said distal end wall are joined together; and said guide passage also having a straight portion extending along said second side wall.

7. A surgical stapler according to claim 6, in which a projection is formed on said flexible portion of said urging member, said resilient member comprising a helical spring disposed inwardly of said curved portion of said guide passage, and one end of said helical spring acting on said projection.

8. A surgical stapler according to claim 6, in which said resilient member comprises a spiral spring, a container portion being formed on the body inwardly of an adjacent to said curved portion of said guide passage, said spiral spring being accommodated within said container portion, and one end of said spiral spring acting on the other end of said urging member remote from said staples.

9. A surgical stapler comprising:
(a) an elongated body;
(b) an anvil mounted on a distal end portion of said body;
(c) means for supporting a number of staples disposed in contiguous relation to one another and for guiding said staples toward said anvil;
(d) means for urging said staples, supported on said support and guide means, toward said anvil;
(e) a ram mounted on said body so as to be movable toward and away from said anvil along a straight path extending along a longitudinal axis of said body, a leading one of said staples being disposed in said path and being disposed between said ram and said anvil;
(f) a lever pivotally connected at its proximal end to a proximal end portion of said body so as to be pivotally movable toward and away from said body, said lever having a manipulating portion at its distal end portion for pivotally moving said lever; and
(g) means for converting the pivotal movement of said lever into a rectilinear movement of said ram along said path; said converting means moving said ram toward said anvil when said manipulating portion of said lever is moved toward said body, so that said ram cooperates with said anvil to deform opposite ends of said leading staple toward each other; a direction of movement of said manipulating portion of said lever toward said body being the same as a direction of deformation of said opposite end of said staple toward each other.

10. A surgical stapler according to claim 9, in which said stapler has a size such that said stapler can be disposed in a generally triangular space formed by a thumb and index finger of a hand of an operator of said stapler with said proximal end of said body being disposed at a fork portion where the thumb and the index finger of the hand of the operator are joined together, the thumb being held against said manipulating portion of said lever and the index finger being held against said body.

11. A surgical stapler according to claim 2, in which said body has a length of not more than 9 cm, the length of said lever being not more than the length of said body.

* * * * *